United States Patent
Siripragada et al.

(10) Patent No.: US 10,399,942 B2
(45) Date of Patent: Sep. 3, 2019

(54) PROCESS AND NOVEL POLYMORPHIC FORM OF APREMILAST

(71) Applicant: Alembic Pharmaceuticals Limited, Vadodara (IN)

(72) Inventors: Mahender Rao Siripragada, Hyderabad (IN); Dinesh Panchasara, Palanpur (IN); Ilesh Patel, Vadodara (IN); Bhavesh Prajapati, Vadodara (IN); Ankit Shah, Vadodara (IN); Ananda Babu Thirunavakarasu, Vadodara (IN); Pinky Parikh, Vadodara (IN)

(73) Assignee: Alembic Pharmaceuticals Limited, Vadodara (IN)

( * ) Notice: Subject to any disclaimer, the term of this patent is extended or adjusted under 35 U.S.C. 154(b) by 0 days.

(21) Appl. No.: 15/777,427

(22) PCT Filed: Jul. 29, 2016

(86) PCT No.: PCT/IB2016/054540
§ 371 (c)(1),
(2) Date: May 18, 2018

(87) PCT Pub. No.: WO2017/085568
PCT Pub. Date: May 26, 2017

(65) Prior Publication Data
US 2018/0327356 A1    Nov. 15, 2018

(30) Foreign Application Priority Data
Nov. 19, 2015 (IN) .......... 4347/MUM/2015
Mar. 27, 2016 (IN) .............. 201621010410

(51) Int. Cl.
*C07D 209/36* (2006.01)
*C07D 209/48* (2006.01)
*C07C 315/04* (2006.01)
*C07C 317/28* (2006.01)
*C07D 207/28* (2006.01)
*A61K 31/00* (2006.01)
(Continued)

(52) U.S. Cl.
CPC ............ *C07D 209/48* (2013.01); *A61K 31/00* (2013.01); *C07C 33/22* (2013.01); *C07C 315/04* (2013.01); *C07C 315/06* (2013.01); *C07C 317/28* (2013.01); *C07D 207/28* (2013.01); *C07B 2200/07* (2013.01); *C07B 2200/13* (2013.01)

(58) Field of Classification Search
CPC ... C07C 315/66; C07C 33/22; C07B 2200/07; A61K 31/00
USPC ......................................... 548/485
See application file for complete search history.

(56) References Cited

U.S. PATENT DOCUMENTS 6,020,358 A   2/2000  Muller et al.
6,962,940 B2  11/2005 Muller
(Continued)

OTHER PUBLICATIONS

Rowe et al, Handbook of Pharmaceutical Excipients, 6th ed., 2009, cover sheet, p. 64. (Year: 2009).*

*Primary Examiner* — Taylor V Oh
(74) *Attorney, Agent, or Firm* — Sheppard Mullin Richter & Hampton LLP

(57) ABSTRACT

The present invention provides an improved process for the preparation of Apremilast using novel intermediates. The present invention also relates to the novel crystalline polymorphic form of Apremilast.

9 Claims, 7 Drawing Sheets

(51) Int. Cl.
  *C07C 33/22*   (2006.01)
  *C07C 315/06*  (2006.01)

(56) References Cited

U.S. PATENT DOCUMENTS

| | | |
|---|---|---|
| 7,208,516 B2 | 4/2007 | Muller |
| 7,276,529 B2 | 10/2007 | Muller |
| 7,427,638 B2 | 9/2008 | Muller |
| 7,893,101 B2 | 2/2011 | Muller |
| 8,093,283 B2 | 1/2012 | Muller |
| 8,629,173 B2 | 1/2014 | Muller |
| 9,018,243 B2 | 4/2015 | Muller |
| 9,433,606 B2 | 9/2016 | Muller |
| 2013/0217918 A1 | 8/2013 | Venkateswaralu et al. |
| 2014/0187599 A1* | 7/2014 | Schafer ................ A61K 9/0014 514/417 |

* cited by examiner

PROCESS AND NOVEL POLYMORPHIC FORM OF APREMILAST

RELATED APPLICATION APPLICATIONS

This application is a national stage application filed under 35 U.S.C. § 371 of International Application No. PCT/IB2016/054540, filed Jul. 29, 2016, which claims the benefit of, and priority to, Indian patent application numbers IN4347/MUM/2015, filed Nov. 19, 2015, and IN201621010410, filed on Mar. 27, 2016, all of which are incorporated herein by reference.

FIELD OF INVENTION

The present invention relates to an improved process for the preparation of Apremilast of formula-I and novel polymorphic forms thereof. The present invention also relates to a process for the preparation of novel intermediates and their use in the preparation of Apremilast.

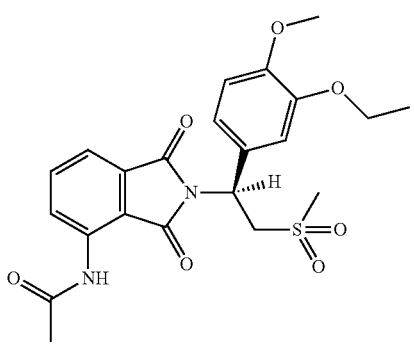

Formula-1

BACKGROUND OF THE INVENTION

Apremilast is a phosphodiesterase 4 (PDE4) inhibitor. Apremilast is chemically known as N-[2-[(1S)-1-(3-ethoxy-4-methoxyphenyl)-2-(methylsulfonyl) ethyl]-2,3-dihydro-1,3-dioxo-1H-isoindol-4-yl]acetamide. Apremilast is indicated for the treatment of adult patients with active psoriatic arthritis. It is available under the trade name of OTEZLA® as an inhibitor of phosphodieasterase 4 (PDE4) and OTEZLA tablets are supplied in 10, 20, and 30 mg strengths for oral administration.

U.S. Pat. No. 6,020,358 discloses racemic 2-[1-(3-ethoxy-4-methoxy phenyl)-2-(methylsulfonyl)ethyl]-2,3-dihydro-1,3-dioxo-1H-isoindol-4-yl]acetamide and process for its preparation, which is incorporated herein by reference.

U.S. Pat. No. 7,427,638 discloses stereomerically pure (+)-2-[1-(3-ethoxy-4-methoxyphenyl)-2-methylsulfonylethyl]-4-acetylaminoisoindoline-1,3-dione, substantially free of its (−) isomer, or a pharmaceutically acceptable metabolite, salt, solvate or hydrate, thereof and its pharmaceutical composition.

International PCT application number WO2009120167 disclose various solid forms including crystal forms and amorphous forms and their mixture comprising one or more of the Forms A, B, C, D, E, F, G and an amorphous solid form. WO2014072259 discloses pharmaceutical composition of amorphous Apremilast with at least one excipients prepared by melt extrusion technique.

CN104761484A discloses the new polymorphic form i.e., form: II.

CN104892486A discloses the new polymorphic form i.e., form: B+.

The present invention provides a process for the preparation of Apremilast using novel intermediates. The process of the present invention can be practiced on an industrial scale, and also can be carried out without sacrifice of overall yield.

The technical problem underlying the present invention is to circumvent the drawbacks of the known crystalline forms of Apremilast disclosed in the state of the art such as toxicity issues of solvates, stability issues of polymorphic forms due to conversation into the other form, bioavailability issues due to limited solubility and preparation issues due to similar crystallization processes; by providing novel polymorphic forms of Apremilast which shows high solubility and is obtained in polymorphically pure form in an easy and reliable manner.

The specific solvate and polymorphic form provided by the present invention possess superior, highly favourable properties appropriate for pharmaceutical development that were not disclosed in the prior art. Further, these solid state forms permit the preparation of pharmaceutical compositions with improved performance characteristics to be prepared.

SUMMARY OF THE INVENTION

The main aspect of the invention is to provide a simple, cost effective process for the preparation of Apremilast and intermediates thereof.

The invention relates to the preparation of Apremilast, a compound of the formula (1) comprising:

a. reacting aldehyde of formula (2) with strong base, lewis acid, dimethyl sulfone, lithium bis(trimethylsilyl)amide in the presence of suitable solvent give compound of formula (3);

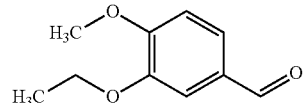

Formula-2

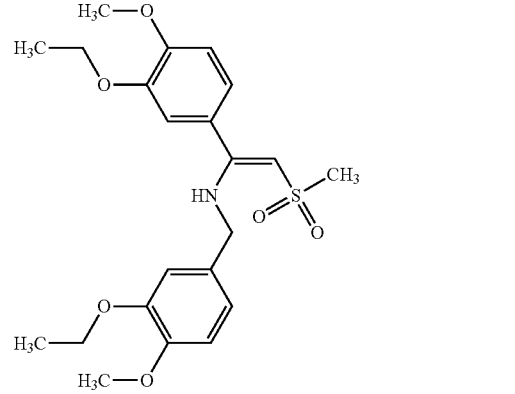

Formula-3 b. reducing compound of formula (3) or salt thereof, to intermediate compound of formula (4), which on further debenzylation gives compound of formula (5);

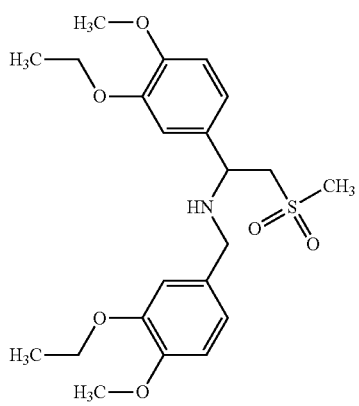

Formula-4

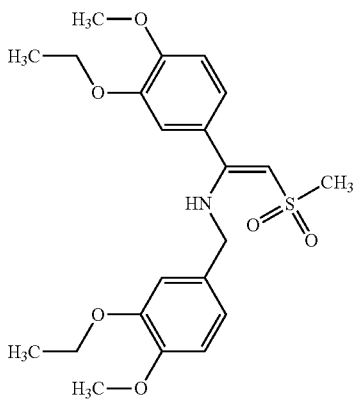

Formula-3

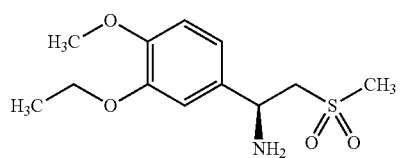

Formula-5 c. resolving compound of formula (5) with resolving agent to give desired enantiomer of chiral amine or its salt;

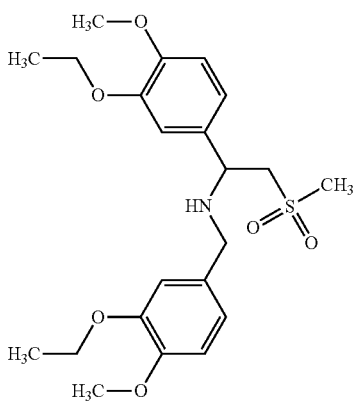

Formula-4

Formula-6 d. condensing compound of formula (6) or its salt with compound of formula (7) in presence of suitable solvent and with or without the use of buffering agent or base gives a compound of formula (1)

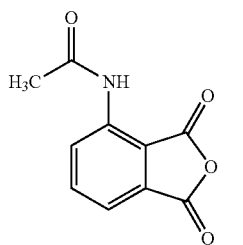

Formula 7

Another aspect of the present invention is to provide compound of formula (3) or a salt, solvate including a hydrate, stereoisomer, or polymorph thereof;

Another aspect of the present invention is to provide compound of formula (4) or a salt, solvate including a hydrate, stereoisomer, or polymorph thereof;

Another aspect of this invention is to provide process for the preparation compound of formula (3) and formula (4). The enamine compound of formula (3), i.e., N-[3-ethoxy-4-methoxymethylbenzene]-1-(3-Ethoxy-4-methoxyphenyl)-2-methyl sulfonyl ethylene amine and a compound of formula (4) i.e., N-[3-ethoxy-4-methoxymethylbenzene]-1-(3-Ethoxy-4-methoxyphenyl)-2-methylsulfonyl ethylamine; such compounds can be used to provide, compound of formula (1).

According to another aspect, there is provided a highly pure apremilast or its solvates or its hydrates thereof substantially free of impurity.

Another aspect of the present invention is to provide novel impurity of Apremilast such as compound of formula A.

Formula: A

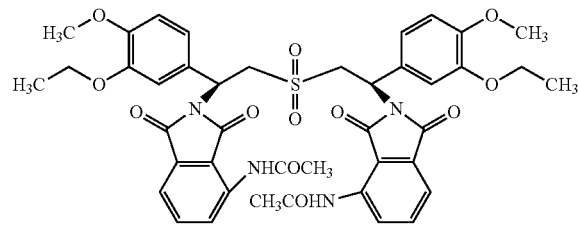

The present inventors also have focused on the problems associated with the prior art polymorphs and have invented novel polymorphic form of Apremilast.

In another aspect present invention relates to a novel crystalline solvates of Apremilast such as benzyl alcohol solvate.

In another aspect present invention provides novel crystalline form Al-1 of Apremilast which is benzyl alcohol solvate of Apremilast and process for preparation thereof.

DETAILED DESCRIPTION OF INVENTION

Figure 1:
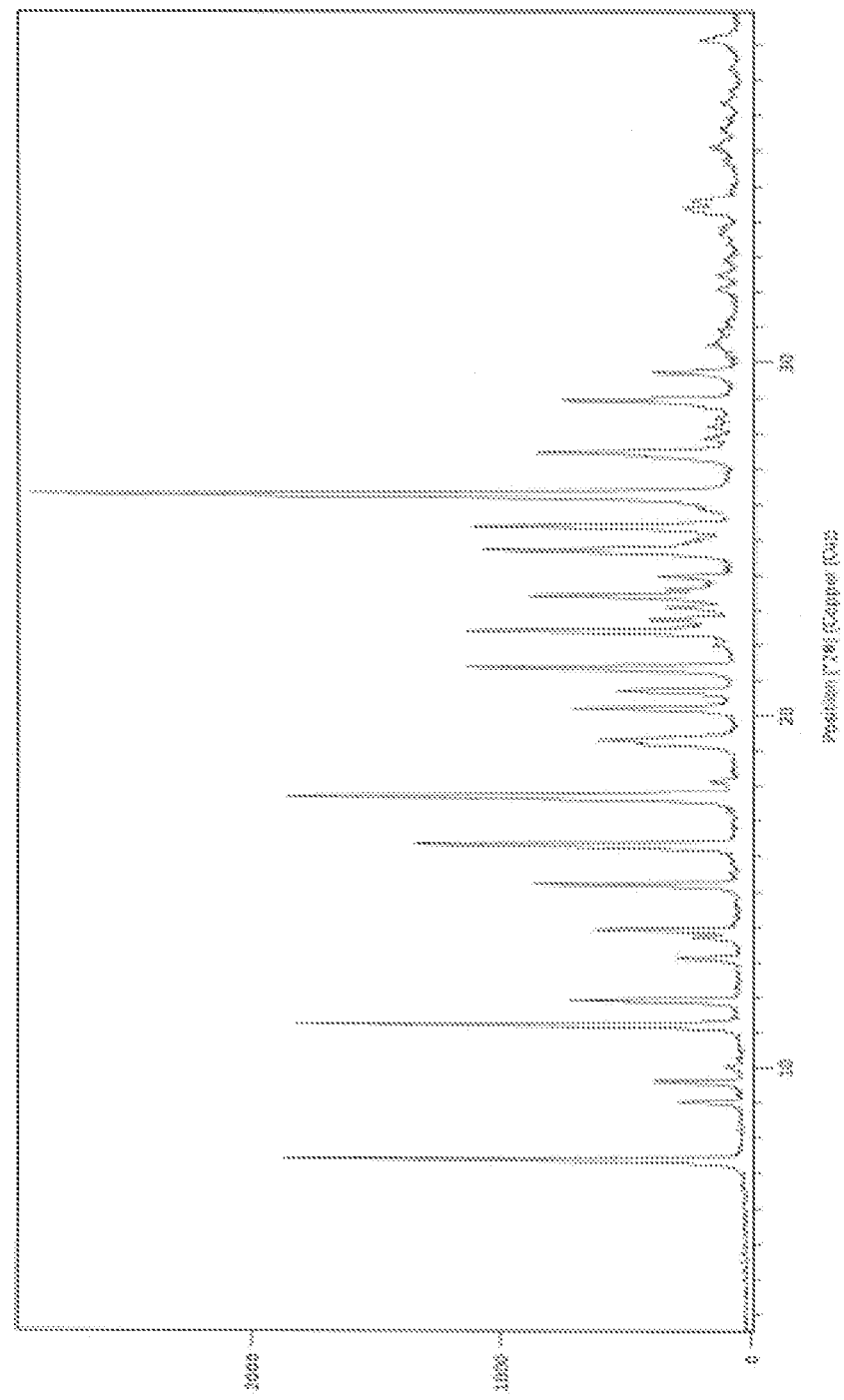
FIG. 1 is an illustration of a Powder X-ray diffraction (PXRD) pattern of Benzyl alcohol solvate of Apremilast.

The present invention provides a process for the preparation of Apremilast and its intermediates thereof with high product yield and quality. In particular, the present invention provides a process for the preparation of Apremilast wherein the process includes the use of novel intermediates; thereby process more convenient and economical, particularly on commercial scale.

As used herein, "comprising" means the elements recited, or there equivalents in structure or function, plus any other elements which are not recited. The terms are also to be constructed as open ended unless the context suggests otherwise.

All ranges recited have included the end points, including those that recite a range between two values.

As used herein and unless otherwise indicated, the term "stereochemically pure" means a composition that comprises one stereoisomer of a compound and is substantially free of other stereoisomers of that compound. A typical stereochemically pure compound comprises greater than about 80% by weight of one stereoisomer of the compound and less than about 20% by weight of other stereoisomers of the compound and most preferably greater than about 97% by weight of one stereoisomer of the compound and less than about 3% by weight of the other stereoisomers of the compound. As used herein and unless otherwise indicated, the term "enantiomerically pure" means a stereochemically pure composition of a compound having one chiral centre.

In one embodiment, the present invention provides an improved method of synthesizing apremilast of formula-1, comprising:
   a. reacting aldehyde of formula (2) with strong base, lewis acid, dimethyl sulfone, lithium bis(trimethylsilyl)amide in the presence of suitable solvent give compound of formula (3);

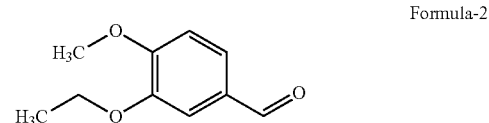
Formula-2

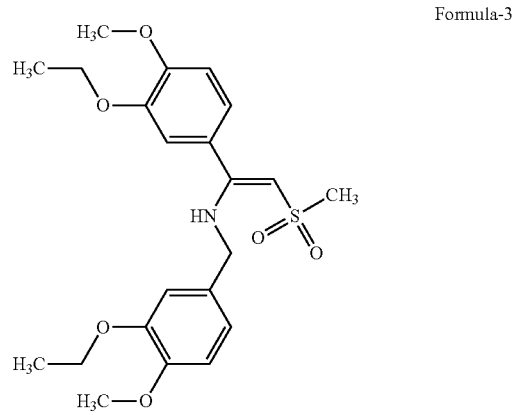
Formula-3 b. reducing compound of formula (3) or salt thereof, to intermediate compound of formula (4), which on further debenzylation gives compound of formula (5)

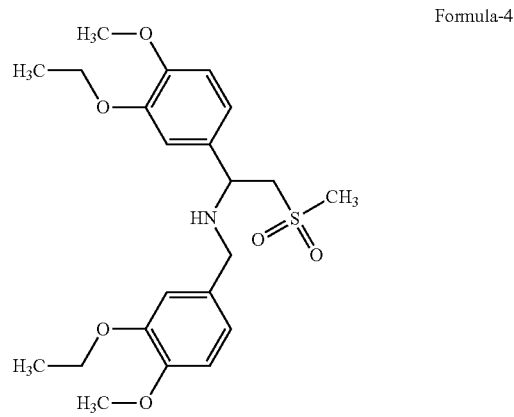
Formula-4

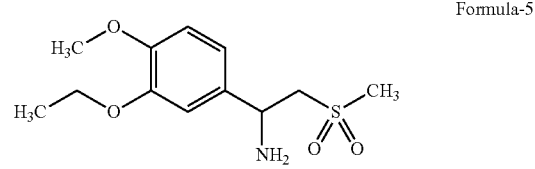 [SMILES: CCOc1cc([C@H](N)CS(C)(=O)=O)ccc1OC]
Formula-5 c. resolving compound of formula (5) with resolving agent to give desired enantiomer of chiral amine or its salt Formula-6

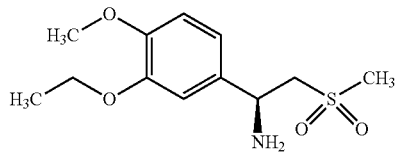

d. condensing compound of formula (6) or its salt with compound of formula (7) in presence of acidic medium and with or without the use of buffering agent or base gives a compound of formula (1), Formula 7

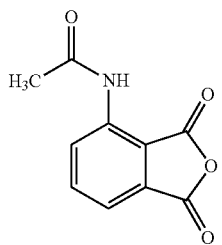

Step (a) involves reacting aldehyde of formula (2) with strong base, lewis acid, dimethyl sulfone, lithium bis(trimethylsilyl)amide in the presence of suitable solvent give compound of formula (3);

For the reaction of step (a) suitable strong base used in step (a) is selected from n-butyl lithium, sodium hydride, lithium hydride, sodium amide and the like.

Suitable lewis acid used in step (a) is selected from $Et_2AlCl$, $EtAlCl_2$, $BF_3$, anhydrous $CuSO_4$, $FeSO_4$, $SnCl_4$, $AlCl_3$, Ti (isopropoxide)$_4$, $TiCl_4$, Ti (ethoxide)$_4$ and the like.

Suitable solvent used in step (a) is selected from but not limited to, diethyl ether, tetrahydrofuran, N-methyl pyrrolidinone, MTBE, glyme, diglyme, toluene, xylene, hexanes, and mixtures thereof, more specifically in step (a) reaction of aldehyde of formula (2) with n-butyl lithium, $BF_3$ etherate, dimethyl sulfone, Lithium bis(trimethylsilyl)amide and THF give compound of formula (3).

Suitable temperatures for this reaction may be varying from −80° C. to 50° C. The reaction may be carried out for time period ranging from about 30 minutes to about 10 hours or longer.

The product can be isolated from the reaction mass by quenching the reaction mixture in cold water and the separated solid was filtered and washed to give pure compound N-[3-ethoxy-4-methoxymethylbenzene]-1-(3-ethoxy-4-methoxy phenyl)-2-methylsulfonylethenamine of formula (3).

Step (b) involves reducing compound of formula (3) or salt thereof, to intermediate compound of formula (4), which on further debenzylation gives compound of formula (5)

In step (b) reduction of compound of formula (3) or salt thereof, in presence of any reducing agent known in the art for reduction of double bond can be used here.

Suitable reducing agent used in step (b) is selected using the suitable transition metal catalyst which is further selected from copper, nickel, palladium, platinum, rhodium, iridium, and ruthenium. In one embodiment reducing agent is metal catalyst such as Pd on carbon in presence of hydrogen gas pressure.

Optionally the reduction can occur in presence of an acid source such as but not limited to acetic acid, methane sulfonic acid, trifluoro acetic acid, p-toluene sulfonic acid, 4-(trifluoromethyl) benzoic acid, hydrochloric acid, nitric acid, sulphuric acid, phosphoric acid and mixtures thereof. In one embodiment the acid source is p-toluene sulfonic acid. The reduction can occur in a solvent such as, but not limited to ethyl acetate, diethyl ether, tetrahydrofuran, acetic acid, acetonitrile, N-methyl pyrrolidinone, dimethyl formamide, dimethyl sulfoxide, water and mixtures thereof. In one embodiment, the solvent is a mixture of ethyl acetate and water.

The suitable temperatures for reduction step may be about 0° C. to about reflux temperature of the solvent. The reduction is generally performed until the reaction is substantially complete.

Reduction of compound of formula (4) is subsequently followed by debenzylation to give compound of formula (5). Debenzylation also can occur using the same reagents and conditions which is used during reduction or in presence of any debenzylating agent known in the art can be used here.

Step (c) involves resolution of compound of formula (5) occurs with resolving agent in suitable solvent to give desired enantiomer of chiral amine with its complex/salt. Generally chiral amido acid is used to resolve compound of formula (5) to give salt of desire enantiomer in suitable solvent.

Chiral amido acid is an acid in which a portion of the non-acid hydrogen has been replaced by the amido group such as but not limited to, L isomers of pyro glutamic acid, N-acetyl-proline, N-benzyl-pyroglutamic acid.

Suitable solvents are selected from but not limited to chloroform, carbon tetrachloride, methylene chloride, and the like; alcohols such as methanol, ethanol, propanol and the like; ketones such as acetone, 2-butanone and the like; esters such as ethyl acetate, butyl acetate and the like; straight or branched chain $C_5$-$C_{10}$ hydrocarbons such as n-hexane, cyclohexane and the like; ethers such as diethyl ether, tetrahydrofuran and the like and other organic solvents such as acetonitrile and Dimethyl formamide, DMSO, water or mixtures thereof. A specific chiral amido acid used here is L-pyro glutamic acid and suitable solvent is mixture of acetone and methanol.

The suitable temperatures for resolution step may be about 0° C. to about the reflux temperature of the solvent. The reaction may be carried out for time periods ranging from about 30 minutes to about 10 hours longer.

Optionally the compound of formula (5) can be further purified by a repeated resolution, crystallization and combination of thereof to enhance the chiral purity.

Typically the product obtained by the above described method contains about 90 wt % of the desired enantiomer. The purity of the product can be increased to about 99 wt % by recrystallization. Acetone and methanol mixture is the preferred recrystallization solvent.

Neutralizing of the salt of compound of formula 6 comprises treating the purified salt with a base, preferably an aqueous solution of a base. The base that can be used is selected from the group of inorganic bases such as sodium hydroxide, potassium hydroxide, sodium carbonate, potassium carbonate, sodium bicarbonate, potassium bicarbonate, sodium methoxide, potassium methoxide and the like; organic bases such as liquid ammonia, triethylamine, diisopropylethylamine, pyridine and the like; aqueous or alcoholic mixtures thereof. Preferably aqueous sodium hydroxide. Once a sufficient quantity of neutralizing base has been reacted with the salt, the liberated chiral amine is extracted in water immiscible solvent such as dichloro methane, toluene or ethyl acetate. The organic solvent is removed by distillation and obtained chiral pure amine which can further crystallise in the suitable solvent such as methanol.

In one more embodiment unwanted isomer of compound of formula-6 can be racemised to convert in compound of formula-5 and again resolved to get desired isomer. Racemisation can be done for unwanted isomer of compound of formula-6 or first convert it in to nitro compound and then racemise.

Step (d) involves condensation of compound of formula (6) or its salt with compound of formula (7) in presence of suitable solvent and with or without the use of buffering agent or base gives a compound of formula (1).

Suitable solvent for condensation is acetic acid. The suitable temperature for condensation step may be about 0° C. to about reflux temperature of the solvent. The reaction may be carried out for time periods ranging from about 30 minutes to about 10 hours longer.

In another embodiment step (d) reaction time is 1-2 hours in presence of the buffering agent or base. The suitable buffer used is sodium acetate. The suitable base used is triethyl amine. Use of acetic anhydride or acetyl chloride in step (d) has advantages. It increases the yield of final API as well as decreases the amount of impurity in the final product.

The compounds at any stage of the process of the present invention may be recovered from a suspension/solution using any techniques such as decantation, filtration by gravity or by suction, centrifugation, slow evaporation, and the like or any other suitable techniques. The solids that are isolated may be carry a small proportion of occlude mother liquor containing a higher percentage of impurities and the resulting wet solids may be optionally be suction dried.

In one embodiment, the present invention provides a process for the preparation of compound of formula-I as represented schematically in scheme I as shown below.

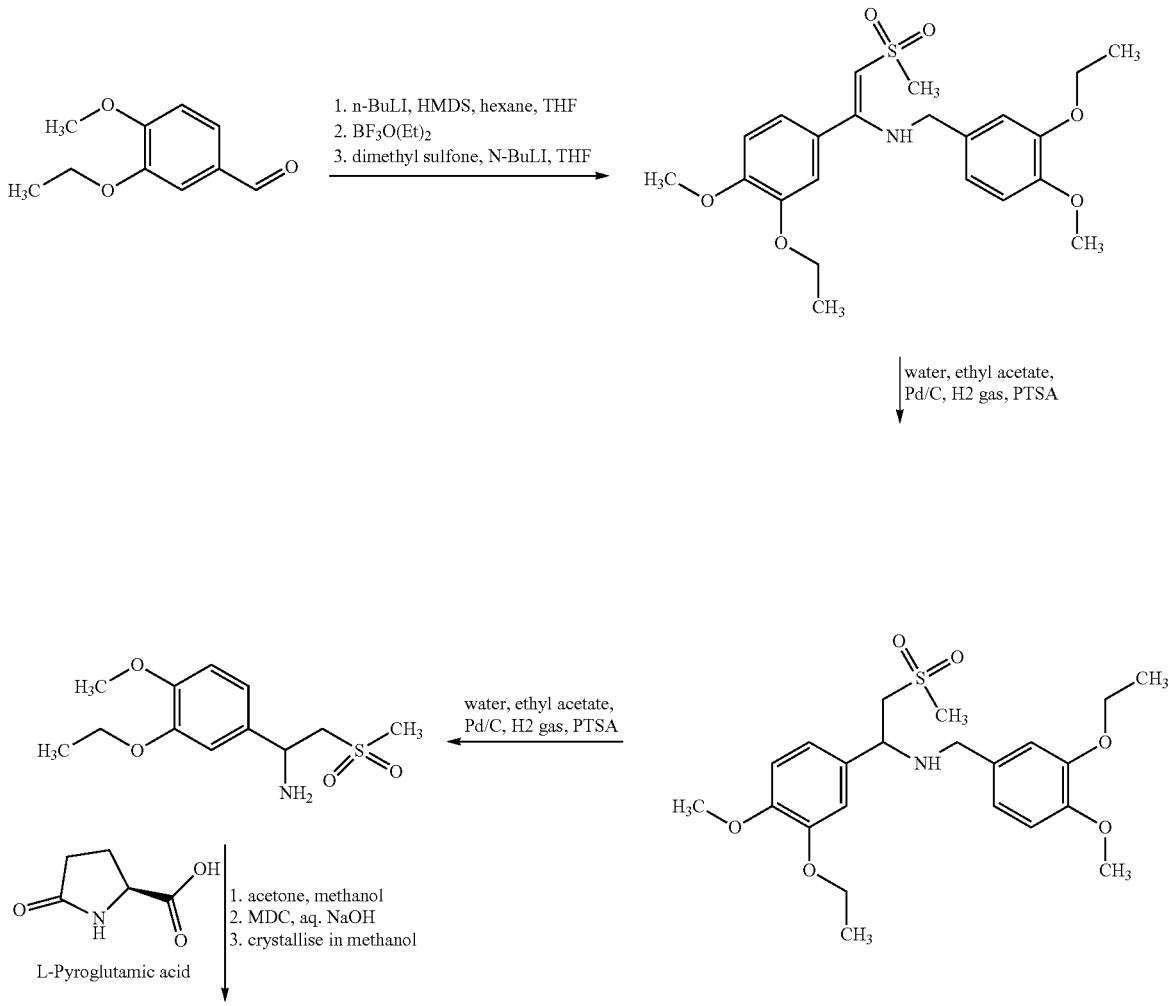

Scheme 1

-continued

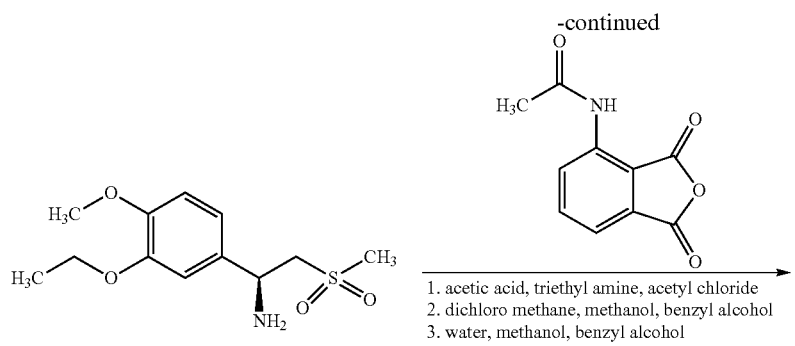

1. acetic acid, triethyl amine, acetyl chloride
2. dichloro methane, methanol, benzyl alcohol
3. water, methanol, benzyl alcohol

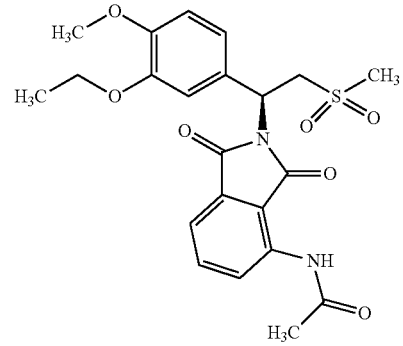

According to another aspect, there is provided isolated Apremilast impurities. The present inventors have surprisingly found that the impurities are formed as during the synthesis of apremilast due to chemical instability of the target substance and due to possible side reactions. The novel impurity of Apremilast is isolated, synthesized and characterized, which is mentioned as below.

Formula: A

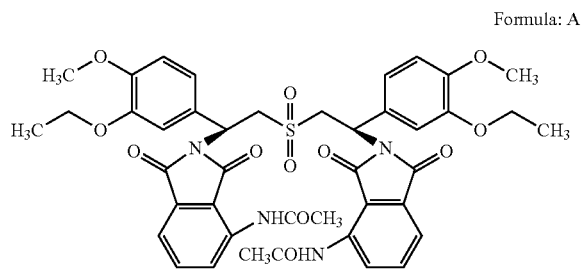

According to another aspect, a method of testing the purity of a sample of Apremilast or its salt or a pharmaceutical dosage form comprising Apremilast, which method comprises analysing the said sample for the presence of compound of formula A.

According to another aspect, Apremilast having a content of compound of formula A less than 0.3% by mole.

Extensive experimentation was carried out by the present inventors to reduce the level of the impurities in Apremilast. As a result, it has been found that the where the impurities formed in the preparation of the Apremilast can be reduced or completely removed.

As used herein, "highly pure Apremilast or its solvates or its hydrates thereof substantially free of impurity" refers to Apremilast or its solvates or its hydrates thereof comprising above mentioned impurity or its salt thereof in an amount of less than about 0.15% as measured by HPLC. Specifically, the Apremilast, as disclosed herein, contains less than about 0.10%, more specifically less than about 0.05%, still more specifically less than about 0.02% of impurity, and most specifically is essentially free of impurity.

In addition to the presence of impurities, the solid state physical properties of an active pharmaceutical ingredient (API), can be very important in formulating a drug substance, and can have profound effects on the ease and reproducibility of formulation.

According to another aspect, there is provided a highly pure Apremilast or its solvates or its hydrates thereof substantially free of impurities.

A polymorphic form may be referred to herein as being characterized by graphical data "as shown in" a Figure. Such data include, for example, powder X-ray diffractograms. The graphical data potentially provides additional technical information to further define the respective solid state form which can not necessarily be described by reference to numerical values or peak positions. In any event, the skilled person will understand that such graphical representations of data may be subject to small variations, e.g., in peak relative intensities and peak positions due to factors such as variations in instrument response and variations in sample concentration and purity, which factors are well known to the skilled person. Nonetheless, the skilled person would readily be capable of comparing the graphical data in the Figures herein with graphical data generated for an unknown crystal form and confirming whether the two sets of graphical data characterize the same solid state form or two different solid state forms. The skilled person would understand that a solid state form referred to herein as being characterized by graphical data "as shown in" a Figure would include any solid state form of the same chemical characterized by graphical data substantially similar to the Figure except for such small variations, the potential occurrence of which is well known to the skilled person.

In another embodiment; the present invention encompasses the solvates isolated in pure form or when admixed with other materials, for example other isomers and/or polymorphic forms and/or salt forms or any other material.

Solvates have some variability in the exact molar ratio of their components depending on a variety of conditions understood to a person of skill in the art. For example, a molar ratio of components within a solvate provides a person of skill in the art information as to the general relative quantities of the components of the solvate and in many cases the molar ratio may vary by about plus or minus 20% from a stated range. For example, a molar ratio of 1:1 is understood to include the ratio 1:0.8 as well as 1:1.2 as well as all of the individual ratios in between.

The present invention relates to solvates of Apremilast with benzyl alcohol, propylene glycol, dimethyl sulphoxide and anisole. In another embodiment present invention relates to a novel crystalline solvates of apremilast such as benzyl alcohol solvate and anisole solvate. In another embodiment present invention provides novel crystalline form Al-1 of Apremilast which is benzyl alcohol solvate of apremilast.

In specific embodiment the present invention relates to a crystalline benzyl alcohol solvate of apremilast wherein the molar ratio of apremilast to benzyl alcohol is approximately 1:0.3~1:1.1; more specifically, crystalline Apremilast benzyl alcohol solvate 1:0.5. The crystalline solvates of the present invention may have advantages relative to other known forms of aApremilast including chemical stability, polymorphic stability and/or varying solubility.

In certain embodiments, crystalline form Al-1 of apremilast benzyl alcohol solvate may be characterized by an X-ray powder diffraction analysis. A representative XRPD pattern of crystalline form Al-1 of apremilast benzyl alcohol solvate is provided in FIG. 1. In certain embodiments, crystalline form Al-1 of apremilast benzyl alcohol solvate is characterized by XRPD peaks approximate positions: 7.4, 9.01, 9.59, 11.20, 11.87, 13.91, 15.20, 16.33, 17.65, 19.27, 20.18, 20.66, 21.33, 22.39, 23.39, 24.70, 25.36, 26.25, 27.45, 28.92 and 29.70 degrees 2θ.

Figure 2:
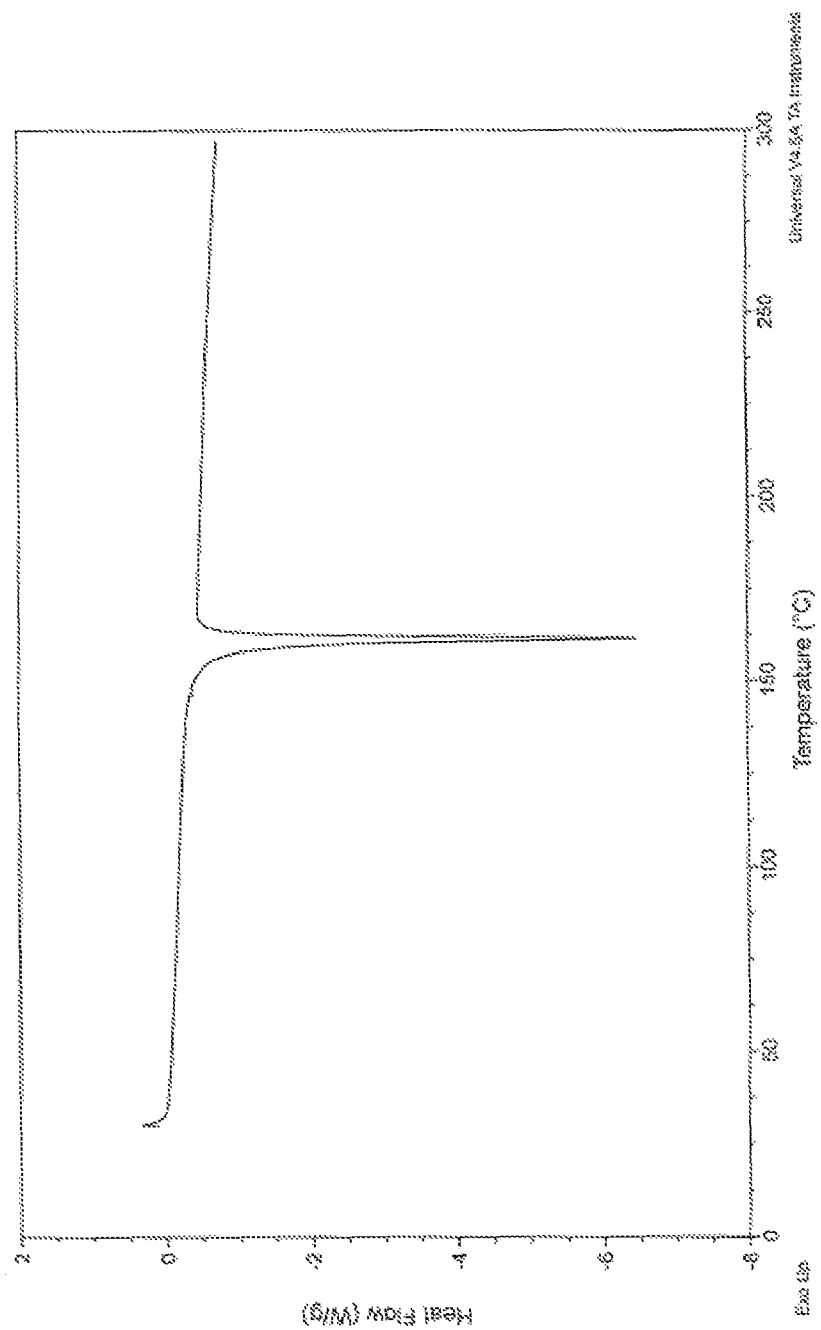
FIG. 2 is an illustration of a Differential scanning calorimetry of Benzyl alcohol solvate of Apremilast.
Figure 3:
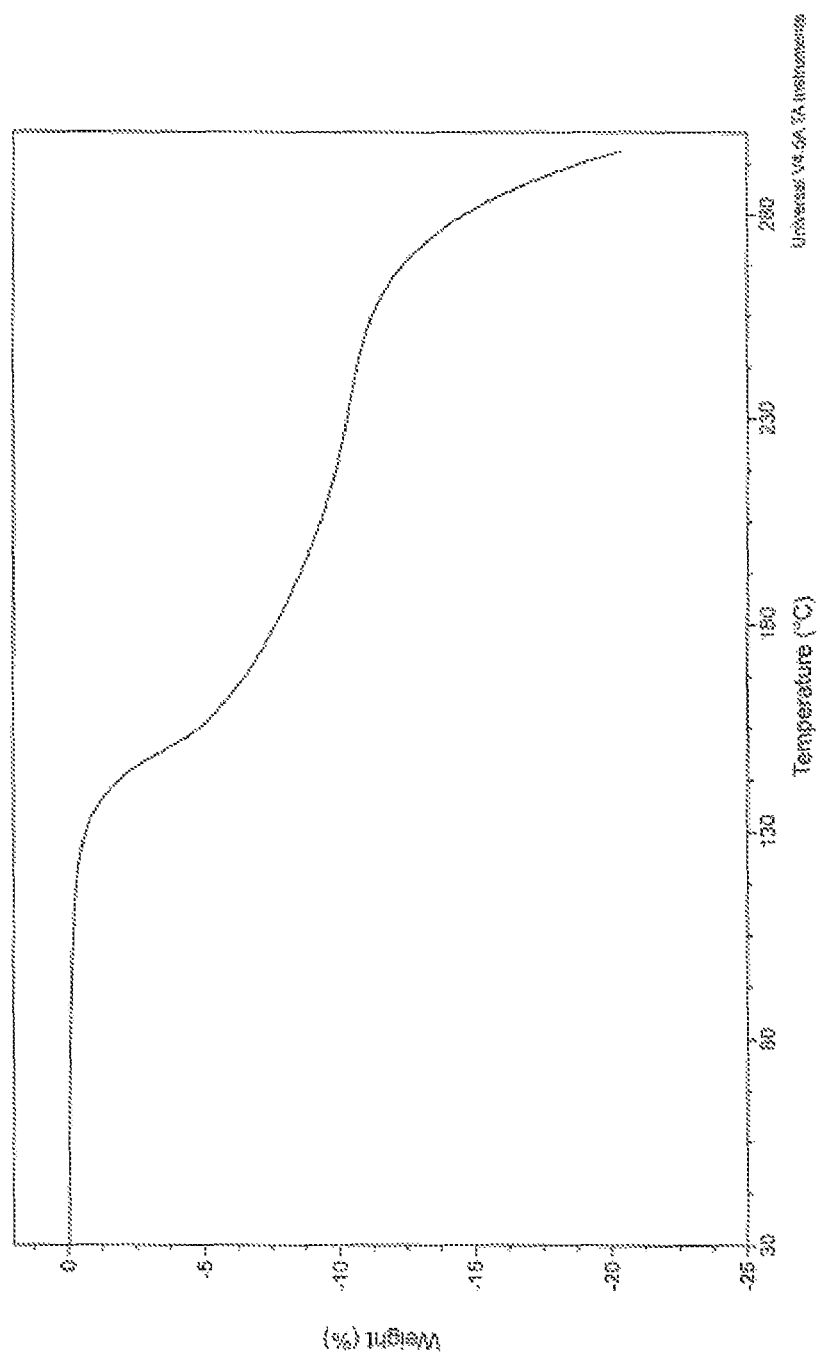
FIG. 3 is an illustration of a Thermogravimetric analysis of Benzyl alcohol solvate of Apremilast
Figure 4:
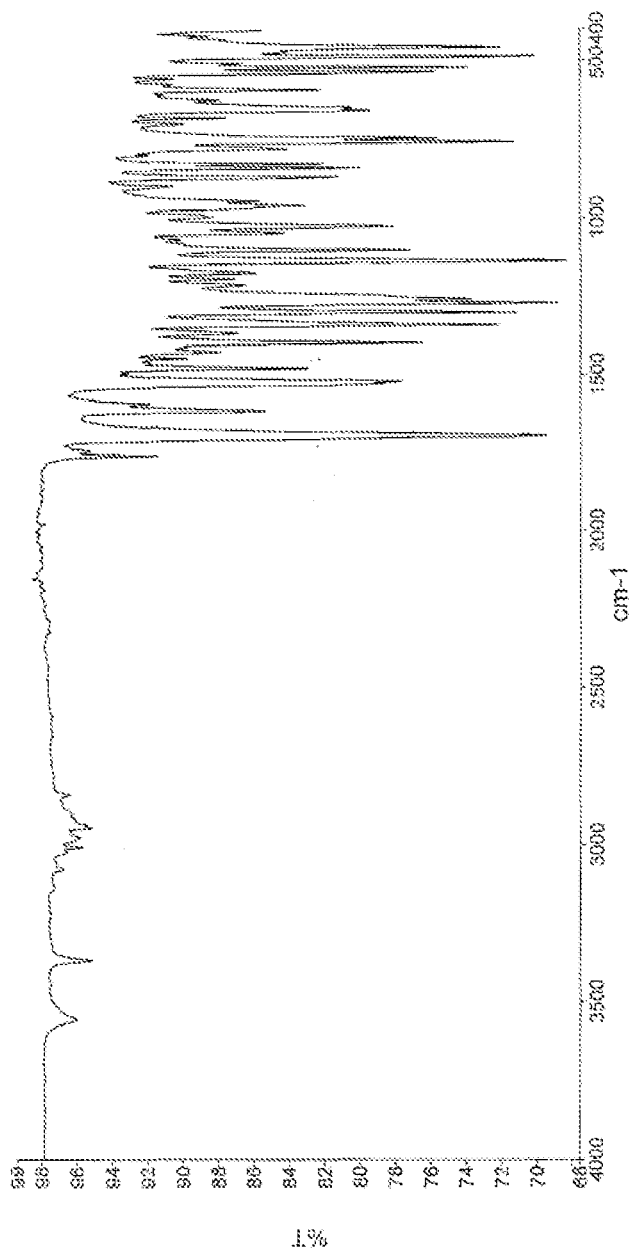
FIG. 4 is an illustration of an IR analysis of Benzyl alcohol solvate of Apremilast
Figure 5:
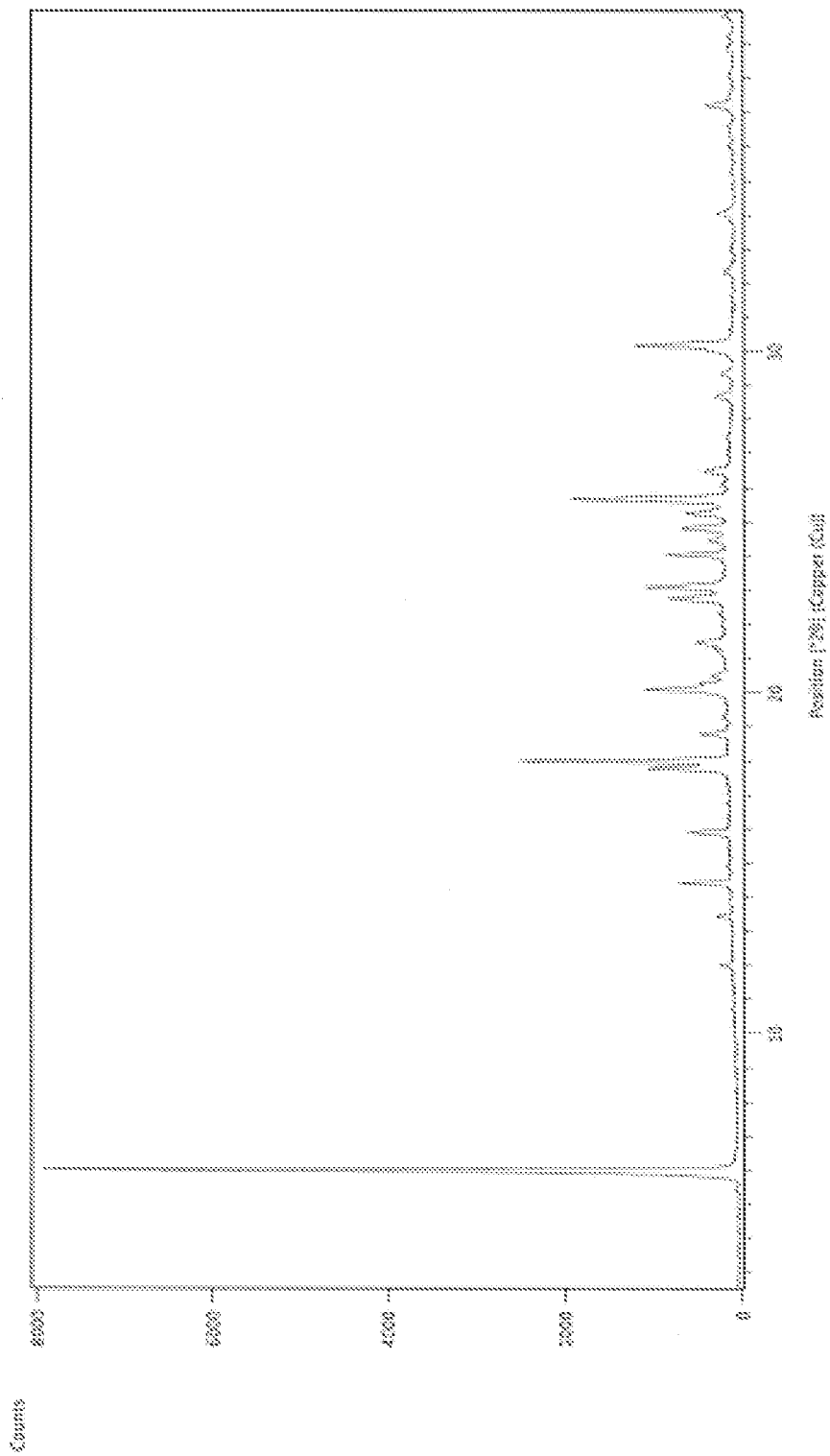
FIG. 5 is an illustration of a Powder X-ray diffraction (PXRD) pattern of (RS)-1-(3-Ethoxy-4-methoxyphenyl)-2-Methylsulfonylethylamine.
Figure 6:
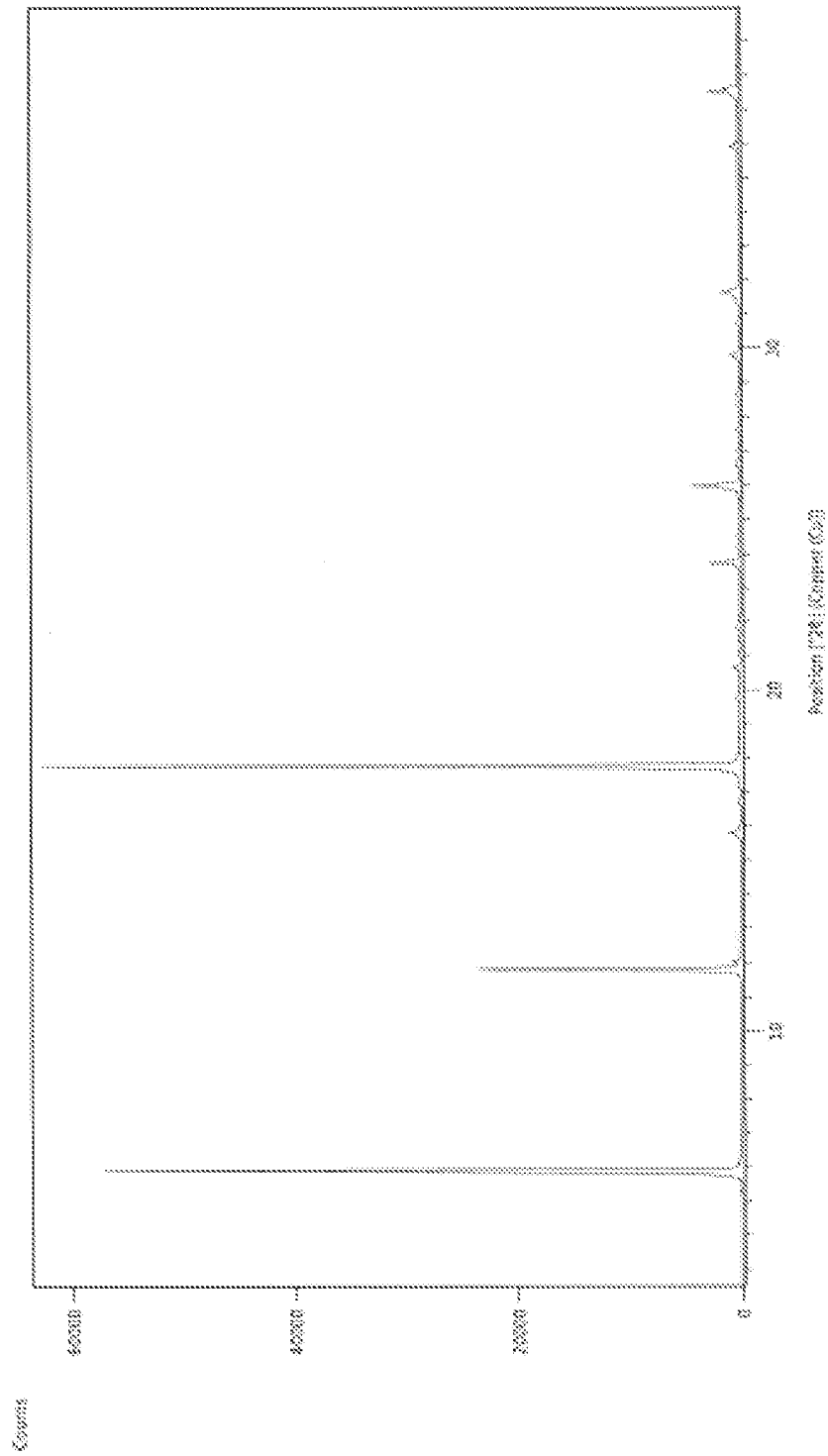
FIG. 6 is an illustration of a Powder X-ray diffraction (PXRD) pattern of (S)-1-(3-Ethoxy-4-methoxyphenyl)-2-Methylsulfonylethylamine.
Figure 7:
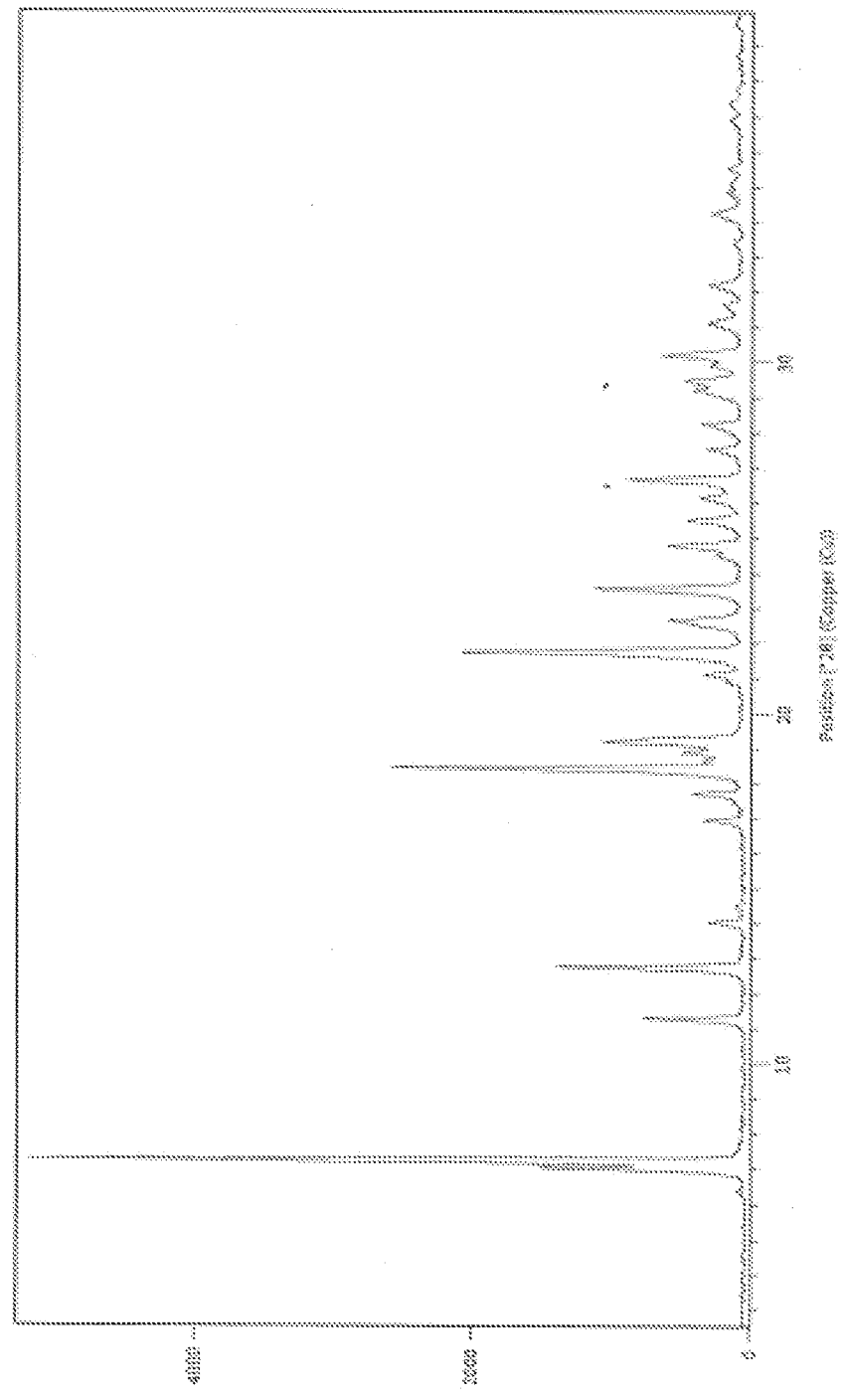
FIG. 7 is an illustration of a Powder X-ray diffraction (PXRD) pattern of (S)-1-(3-Ethoxy-4-methoxyphenyl)-2-Methylsulfonylethylamine-L-pyro glutamic acid salt.

In certain embodiments, crystalline form Al-1 of apremilast benzyl alcohol solvate may be characterized by thermal analysis. A representative DSC plot for crystalline form Al-1 of apremilast benzyl alcohol solvate is shown in FIG. 2. In certain embodiments, crystalline form Al-1 of apremilast benzyl alcohol solvate is characterized by a DSC plot comprising an endothermic event with an onset temperature of about 161.20° C. A representative TGA plot for crystalline form Al-1 of apremilast benzyl alcohol solvate is shown in FIG. 3. In certain embodiments, Form Al-1 is characterized by a TGA plot comprising a mass loss of less than about 22%, e.g., about 10.5%, of the total mass of the sample upon heating from about 25° C. to about 300° C.

The melting points are measured using Differential Scanning Calorimetry (DSC). The equipment is a TA-Instruments DSC-Q1000 calibrated at 10°/min to give the melting point as onset value. About 2 mg of sample is heated 10°/min in a loosely closed pan under nitrogen flow.

Thermo gravimetric analysis (TGA) used for estimation of solvent/water content of dried material is performed using a TA-instruments TGA-Q500 about 10 mg sample is heated 10°/min in an open pan under nitrogen flow.

X-Ray powder diffractograms were measured on a PANalytical X'Pert PRO X-Ray Diffractometer using CuKα1 radiation. The samples were measured in reflection mode in the 2θ-range 2.5-40° using an X' accelerator detector.

In another embodiment crystalline form Al-1 can be obtained by crystallisation from a solvent system comprising benzyl alcohol.

In certain embodiments, crystalline form Al-1 may be characterized by its stability profile. In certain embodiments, form Al-1 material is stable, e.g., its XRPD pattern remains substantially unchanged, upon exposure to elevated temperature, upon exposure to elevated humidity, upon exposure to one or more solvents, and/or upon compression. Form Al-1 is substantially nonhygroscopic.

In certain embodiments, form Al-1 is stable with respect to humidity. Certain embodiments herein provide form Al-1 of compound A which is substantially pure.

In certain embodiments, process for preparing benzyl alcohol solvate of Apremilast comprising;
 a. providing a solution of Apremilast in benzyl alcohol solvent;
 b. isolating Apremilast benzyl alcohol solvate from the solution.

Providing a solution of Apremilast in benzyl alcohol solvent means the solution of Apremilast may be obtained by dissolving Apremilast in benzyl alcohol solvent, or such a solution may be obtained directly from a chemical synthesis mixture in which Apremilast is formed. Providing a solution of Apremilast in benzyl alcohol optionally involves use of other suitable solvents capable of dissolving Apremilast. Then optionally, filtering the solvent solution to remove any extraneous matter; and finally isolating by removing the solvent from the solution to afford Apremilast benzyl alcohol solvate. Removal of solvent is accomplished by, for example, filtering the solid, substantially complete evaporation of the solvent, concentrating the solution and filtering the solid.

wherein suitable solvent is selected from water, methanol, ethanol, isopropanol, 2-propanol, 1-butanol, t-butyl alcohol, 1-pentanol, 2-pentanol, amyl alcohol, ethylene glycol, glycerol, acetone, butanone, 2-pentanone, 3-pentanone, methyl butyl ketone, methyl isobutyl ketone, ethyl formate, methyl acetate, ethyl acetate, propyl acetate, t-butyl acetate, isobutyl acetate, toluene, xylene, methylene dichloride, ethylene dichloride, chlorobenzene, acetonitrile, diethyl ether, diisopropyl ether, t-butyl methyl ether, dibutyl ether, tetrahydrofuran, 1,4-dioxane, 2-methoxyethanol, N,N-dimethylformamide, N, N-dimethylacetamide, N-methylpyrrolidone, pyridine, dimethylsulfoxide, sulfolane, formamide, acetamide, propanamide, pyridine, formic acid, acetic acid, propionic acid, hexane, heptanes, cyclohexane, cycloheptane and cyclooctane or mixtures thereof.

In another embodiment the aApremilast disclosed herein for use in the pharmaceutical compositions of the present invention, wherein 90 volume-percent of the particles (D90) have a size of less than or equal to about 500 microns, specifically less than or equal to about 300 microns, more specifically less than or equal to about 200 microns, still more specifically less than or equal to about 100 microns, and most specifically less than or equal to about 15 microns.

A wet cake obtained at any stage of the process may be optionally further dried. Drying may be carried out a tray dryer, vacuum oven, air oven, fluidized bed dryer, spin flash dryer, flash dryer, and the like at atmospheric pressure or under reduced pressure. Drying may be carried out at temperatures less than about 200° C. or about 20° to about 80° C., or about 30° C. to about 60° C. or any other suitable temperatures, at atmospheric pressure or under reduced pressure. The drying may be carried out for any desired times until the desired quality of product is achieved, such as about 30 minutes to about 20 hours or about 1 to about 10 hours. Shorted or longer times also are useful.

The processes of present invention are simple cost effective, ecologically friendly, reproducible, useful on a commercial scale and robust to produce Apremilast with very high chemical and chiral purity.

Certain specific aspects and embodiments of the present application will be explained in greater detail with reference of the following examples, which are provided only for purposes of illustration and should not able constructed as limited the scope of the application in any manner.

EXAMPLES

Example-1: Preparation of N-[3-ethoxy-4-methoxymethylbenzene]-1-(3-Ethoxy-4-Methoxy phenyl)-2-methylsulfonylethenamine

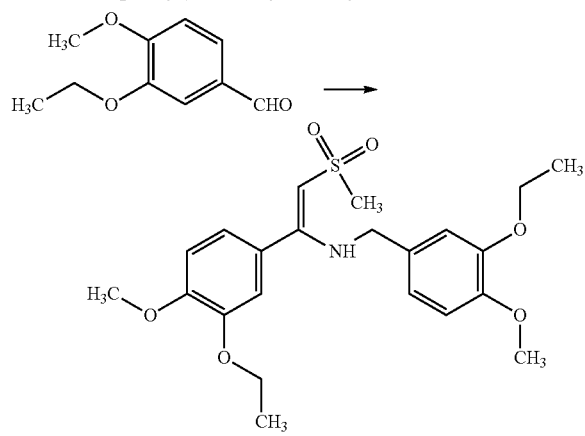

To a stirred solution of Dimethyl sulfone (62.65 g) in tetrahydrofuran (1000 mL) was added n-butyl lithium (2.5 M in Hexane) (169.3 g) under nitrogen at −25±3° C. Reaction mixture was stirred for 60-90 minutes at −5±3° C. In another vessel tetrahydrofuran (300 mL) with n-Butyl Lithium (2.5 M in Hexane) (184.58 g) was stirred at −25±3° C. and Hexamethyldisilazane (HMDS) (116.43 g) was charged at −15 to −5° C. The reaction mixture was then stirred for 25-30 minutes at 22±3° C. and then cooled at −27±3° C. Slowly 3-Ethoxy-4-Methoxy benzaldehyde in tetrahydrofuran (100 g in 200 ml) was added into reaction mass during 15-20 minutes at −27±3° C. and stirred for 15 min. at −27±3° C. Boron trifluoride diethyl etherate [Bf$_3$O(Et)$_2$] (157.52 g) was slowly added into reaction mass during 15-20 min at −27±3° C. and then added earlier prepared sulfone solution during 15-20 min at −27±3° C. Reaction mass was stirred for 60 min at −27±3° C. After completion of reaction process water (50 mL) was added and removed the solvent under vacuum. Finally product was extracted in Dichloromethane which is distilled under vacuum to get desired N-[3-ethoxy-4-methoxymethylbenzene]-1-(3-Ethoxy-4-Methoxy phenyl)-2-methylsulfonylethenamine. MASS: M+1: 436.3, 1H NMR δ (300 MHz, CDCl3): 1.5 (q, 6H), 2.8 (s, 3H), 1.5 (d, 1H), 3.8 (dd, 1H), 3.9 (d, 6H), 4.1 (m, 4H), 4.9 (dd, 1H), 6.9 (m, 4H), 7.1 (t, 1H), 7.4 (s, 1H), 8.1 (s, 1H)

Example-2: Preparation of N-[3-ethoxy-4-methoxymethylbenzene]-1-(3-Ethoxy-4-methoxy phenyl)-2-methylsulfonylethylamine

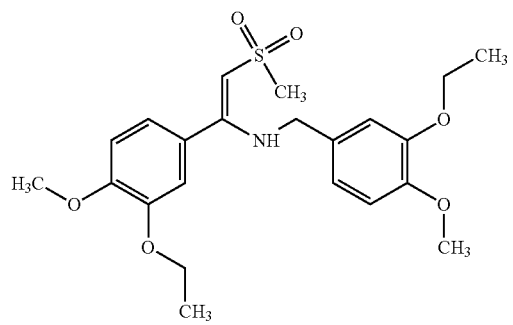

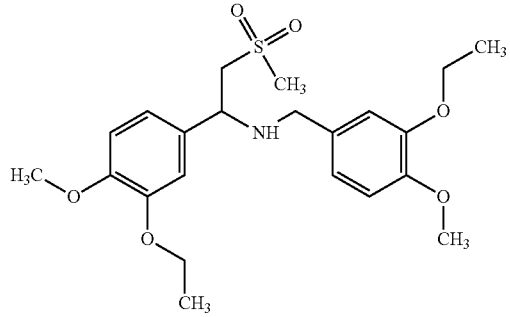

A reaction vessel was charged with N-[3-ethoxy-4-methoxymethylbenzene]-1-(3-Ethoxy-4-methoxyphenyl)-2-methylsulfonylethanamine (62 g). Pd/c (10 g) in methanol (250 ml) was added in to it. Reaction mixture was stirred at 25±3° C. under hydrogen pressure 5-6 Kg for 1 hr. After completion of the reaction, catalyst was filtered and solvent was removed to obtain N-[3-ethoxy-4-methoxymethylbenzene]-1-(3-Ethoxy-4-methoxyphenyl)-2-methylsulfonylethylamine. MASS: M+1: Found, 438.3, 1H NMR δ (300 MHz, CDCl3): 1.4 (q, 6H), 2.6 (s, 1H), 2.7 (s, 2H), 2.8 (s, 1H), 3.1 (dd, 1H), 3.3 (m, 2H), 3.5 (d, 1H), 3.8 (d, 6H), 4.0 (m, 4H), 4.2 (dd, 1H), 6.8 (m, 6H)

Example-3: Preparation of 1-(3-Ethoxy-4-methoxyphenyl)-2-methyl Sulfonyl Ethyl Amine

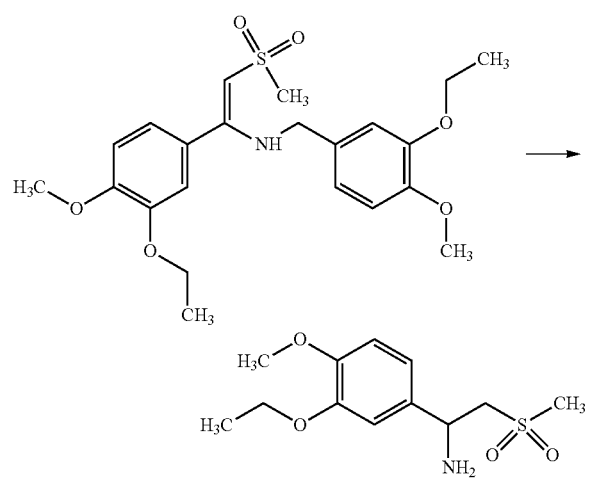

Solution of p-Toluene sulphonic acid in process water (110.83 g in 300 mL) was mixed with the N-[3-ethoxy-4-methoxymethylbenzene]-1-(3-ethoxy-4-methoxyphenyl)-2-methylsulfonylethenamine and was stirred to get clear solution. Ethyl acetate (200 mL) and palladium carbon (10% on carbon) were charged and hydrogenated under H$_2$ gas pressure (6-7 Kg) at 27±3° C. for 2-3 hours. After completion of the reaction; the reaction mass was filtered. Sodium hydroxide solution was charged into the reaction mass to get pH 9-10. The product was extracted in dichloromethane and removed solvent completely to get desired 1-(3-Ethoxy-4-methoxyphenyl)-2-methylsulfonylethylamine.

Example-4: Preparation of (S)-1-(3-Ethoxy-4-methoxyphenyl)-2-methylsulfonylethylamine-L-Pyroglutamic Acid Salt (S-Amine-L-Pyroglutamic Acid Salt)

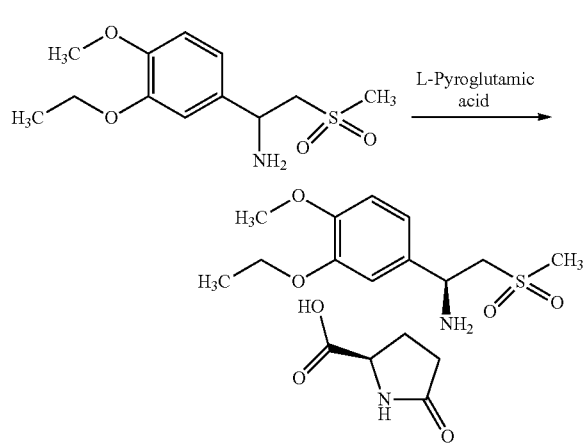

Acetone (300 mL), Methanol (42 mL), racemic Amine (100 g) and L-Pyroglutamic acid (21.51 g) were mixed in to the reaction vessel and heated the reaction mass for 1.0 hr. at 62±3° C. The reaction mass was cooled to room temperature and filtered the solid. The obtained salt was recrystallised in Acetone (240 mL) and Methanol (18 mL) mixture to get desired purity.

Example-5: Preparation of (S)-1-(3-Ethoxy-4-methoxyphenyl)-2-methylsulfonyl Ethylamine (S-Amine)

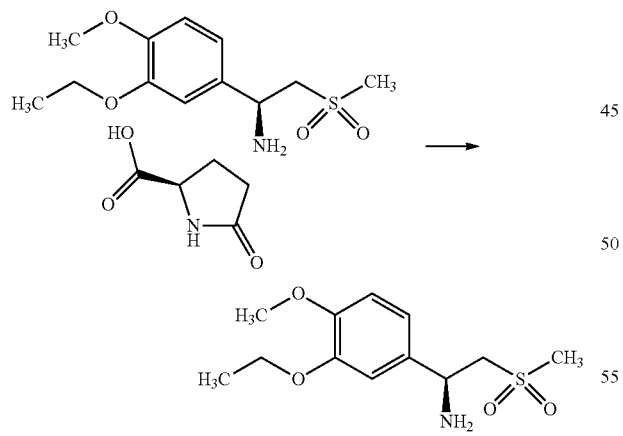

Diasteromeric salt obtained from the above example was mixed with process water (150 mL) and Dichloromethane (150 mL). To this solution was added sodium hydroxide solution slowly to get pH 9-10. The layers were separated and the organic layer was concentrated under reduced pressure. Methanol (60 mL) was charged into residual mass and heated reaction mass for 25-30 minutes at 70±3° C. It was cooled to 7±3° C. and solid was filtered and dried.

Example-6: Preparation of S-2-[1-(3-Ethoxy-4-methoxyphenyl)-2-methylsulfonylethy]-4-acetylaminoisoindoline-1,3-dione (Apremilast Crude)

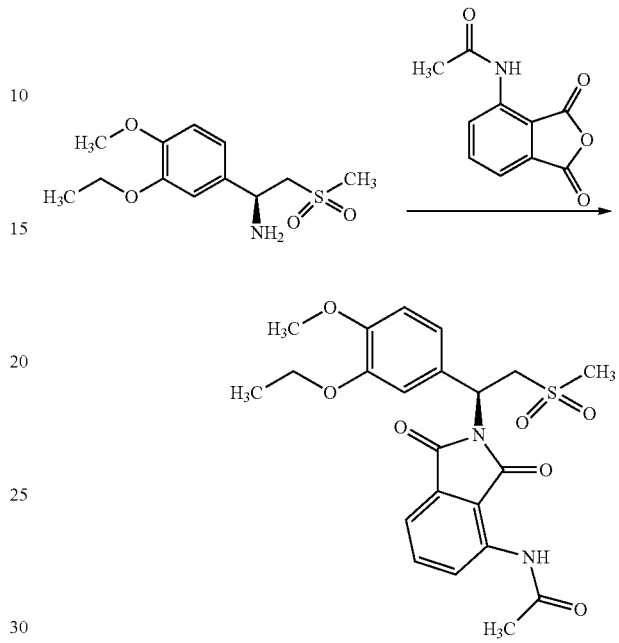

A reaction vessel was charged with glacial acetic acid (300 mL), Tri ethyl amine (40.72 g), (S)-1-(3-Ethoxy-4-methoxyphenyl)-2-methylsulfonylethylamine (100 g) and 3-Acetamido phthalic anhydride (75.05 g). Reaction mass was heated for 1.0 hour at 90±3° C. After completion of the reaction; reaction mass was cooled to 27±3° C. Process water (500 mL) and dichloromethane (300 mL) were added in to the reaction mass. Reaction mass was stirred and settled. Layers were separated. Acetyl chloride (17.23 g) was charged in to the organic layer and was heated for 15-20 min at 40±3° C. The organic layer was cooled to 27±3° C. and washed with sodium bicarbonate solution in water. Benzyl alcohol (118.68 g) was charged into the organic layer and solvent was distilled out completely under reduced pressure at 42±3° C. Methanol (200 mL) was charged into reaction mass at below 40° C. Reaction mass was stirred for 15-20 min. at 52±3° C. and 1 hour at 27±3° C. The solid was filtered and washed with methanol.

Example-7: Preparation of S-2-[1-(3-Ethoxy-4-methoxyphenyl)-2-methylsulfonylethy]-4-acetylaminoisoindoline-1,3-dione (Apremilast Benzyl Alcohol Solvate)

A reaction vessel was added methanol (2500 mL) and apremilast Crude (100 g) and was heated to 67±3° C. till clear solution obtain. Process water (100 mL) and benzyl alcohol (63.04 g) were added in to it at 67±3° C. Reaction mass was stirred for 25-30 minutes at 67±3° C. and then distilled out solvent completely under vacuum. Methanol (1000 mL) was charged and reaction mass was stirred for 25-30 minutes at 67±3° C. The reaction mass was stirred for 1.0 hour at 27±3° C. The solid was filtered and dried.

Example-8: Preparation of S-2-[1-(3-Ethoxy-4-methoxyphenyl)-2-methylsulfonylethy]-4-acetamido isoindoline-1, 3-dione (Acetonitrile Solvate of Apremilast)

A reaction flask was charged with (S)-1-(3-ethoxy-4-methoxyphenyl)-2-methylsulfonylethylamine-L-pyro glutamic acid salt (11 g), 3-acetamidophthalic anhydride (5.6 g), sodium acetate anhydrous (2.5 g) and glacial acetic acid (33 ml). Reaction mixture was heated to 90±3° C. and stirred. After completion of the reaction; reaction mass was cooled to room temperature. Solvent was removed under vacuum and the residue was dissolved in dichloromethane. The resulting organic solution was then washed with water, saturated aqueous sodium bicarbonate solution and brine solution. The organic layer was concentrated under reduced pressure to get residue and that residue was dissolved in acetonitrile to get clear solution and add (0.3~0.5 equivalent) of acetic anhydride. The reaction solution was stirred at 25±3° C. and was filtered to obtain acetonitrile solvate of Apremilast.

Example: 9 Preparation of Amorphous Apremilast

A reaction flask was charged with (S)-1-(3-Ethoxy-4-methoxyphenyl)-2-Methylsulfonylethylamine-N-actyl-L-leucine salt (11 g), 3-acetamidophthalic anhydride (5.3 g), sodium acetate anhydrous (2.0 g) and glacial acetic acid (22 ml). The reaction mixture was heated to 80±3° C. till completion of the reaction. After completion of the reaction, reaction mixture was cooled to room temperature. Solvent was removed under vacuum and the residue was dissolved in ethyl acetate. The resulting organic solution was washed with water, saturated aqueous sodium bicarbonate solution and brine solution. The solvent ethyl acetate was evaporated under vacuum to give amorphous Apremilast which was stirred with cyclohexane and filtered to obtain amorphous Apremilast.

Example: 10 Preparation of Amorphous Apremilast

D M Water (90 ml) and tert.butylamine (125 ml) were charged into the reaction vessel at 27±3° C. The reaction mixture was cooled to −10±3° C. The solution of Apremilast in acetic acid was added by maintaining the reaction temperature. The reaction mixture was stirred for 15-30 minutes at same temperature. The solid was filtered and wet cake was washed with D M Water. Dry the obtained wet cake for 10-12 hrs at 60-80° C. under vacuum.

Example: 11 Preparation of Amorphous Apremilast

A reaction vessel was charged with 5% sodium chloride solution in water (450 ml) was cooled to −10±3° C. The Solution of Apremilast in acetone was added at same temperature and was stirred for 15-30 minutes. The reaction mass filtered and washed the wet cake with D M Water. The obtained wet cake was dried for 10-12 hours at 60-80° C. under vacuum.

Example: 12 Preparation of Amorphous Apremilast

To a reaction vessel was charged 5% ethylene glycol in water (450 ml) at 27±3° C. and was cooled reaction mixture to −10±3° C. The solution of Apremilast in acetone was added at same temperature and was stirred for 15-30 minutes. The reaction mass was filtered and wet cake was washed with D M Water. The obtained wet cake was dried for 10-12 hours at 60-80° C. under vacuum.

The invention claimed is:
1. A crystalline Apremilast benzyl alcohol solvate.
2. The crystalline Apremilast benzyl alcohol solvate according to claim 1, wherein the Apremilast benzyl alcohol solvate is in crystalline form Al-1.
3. The crystalline Apremilast benzyl alcohol solvate of claim 1, wherein the molar ratio of Apremilast to benzyl alcohol is between approximately 1:0.3 and 1:1.1.
4. A crystalline form Al-1 of Apremilast benzyl alcohol solvate having an X-ray powder diffractogram comprising at least one peak at diffraction 2-theta angle selected from 7.40±0.2°, 11.18±0.2°, 16.33±0.2°, 17.65±0.2°, and 26.23±0.2°.
5. The crystalline form Al-1 of Apremilast benzyl alcohol solvate according to claim 2 having a Powder X-ray Diffraction (PXRD) pattern as shown in FIG. 1.
6. The crystalline form Al-1 of Apremilast benzyl alcohol solvate according to claim 2 having a differential scanning calorimetry plot comprising an endothermic peak at 162.2° C.
7. A process for preparing a crystalline benzyl alcohol solvate of Apremilast, the process comprising:
   a. providing a solution of Apremilast in benzyl alcohol solvent; and
   b. isolating Apremilast benzyl alcohol solvate from the solution.
8. A pharmaceutical composition comprising:
   a. the crystalline form Al-1 of Apremilast benzyl alcohol solvate according to claim 2; and
   b. at least one pharmaceutically acceptable carrier, diluent, vehicle or excipient.
9. The crystalline form Al-1 of Apremilast benzyl alcohol solvate according to claim 2, wherein the molar ratio of Apremilast to benzyl alcohol is about 1:0.5.

* * * * *